United States Patent
Diju et al.

(10) Patent No.: US 10,610,142 B1
(45) Date of Patent: Apr. 7, 2020

(54) VIBRATING TOURNIQUET AND METHODS OF COLLECTING BLOOD USING SAME

(71) Applicant: Paulus Holdings Limited, Dublin (IE)

(72) Inventors: Taufeeq Elahi Diju, Dublin (IE); Ronan Ryan, Dublin (IE)

(73) Assignee: Paulus Holdings Limited, Dun Laoghaire (IE)

( * ) Notice: Subject to any disclaimer, the term of this patent is extended or adjusted under 35 U.S.C. 154(b) by 0 days.

(21) Appl. No.: 16/359,186

(22) Filed: Mar. 20, 2019

(51) Int. Cl.
*A61B 5/15* (2006.01)
*A61M 5/42* (2006.01)

(52) U.S. Cl.
CPC .. *A61B 5/150137* (2013.01); *A61B 5/150022* (2013.01); *A61B 5/150083* (2013.01); *A61M 5/422* (2013.01); *A61B 5/1411* (2013.01); *A61B 5/150167* (2013.01); *A61B 5/150412* (2013.01)

(58) Field of Classification Search
CPC ........ A61B 5/150022; A61B 5/150053; A61B 5/150083; A61B 5/150137; A61B 17/12; A61B 17/132; A61B 2017/00438; A61B 2017/0042; A61B 2017/00442; A61B 5/6824; A61B 5/6825; A61B 5/6826; A61F 5/41; A61F 5/05866; A61F 5/05875; A61H 23/00; A61H 19/00; A61H 19/30; A61H 19/32; A61H 19/34; A61H 19/50; A61H 11/00; A61M 5/42; A61M 5/422; A61M 5/425; A41B 2400/322

See application file for complete search history.

(56) References Cited

U.S. PATENT DOCUMENTS

| 4,887,594 A | * | 12/1989 | Siegel | A61M 35/10 601/71 |
| 6,203,509 B1 | * | 3/2001 | Duboff | A61H 23/0263 601/138 |
| 8,206,336 B2 | | 6/2012 | Shantha | |
| 9,333,144 B2 | | 5/2016 | Baxter et al. | |

(Continued)

FOREIGN PATENT DOCUMENTS

WO WO-2009081405 A2 7/2009
WO WO-2016178952 A1 11/2016

OTHER PUBLICATIONS

Baxter, et al., "An Integration of Vibration and Cold Relieves Venipuncture Pain in a Pediatric Emergency Department," https://www.ncbi.nlm.nih.gov/pubmed/22134226, Pediatric Emergency Care, vol. 27, No. 12, Dec. 2011, pp. 1151-1156.

(Continued)

*Primary Examiner* — Darwin P Erezo
*Assistant Examiner* — Christian D Knauss
(74) *Attorney, Agent, or Firm* — Goodwin Procter LLP

(57) ABSTRACT

A device and method for collecting blood from a mammalian digit, the device including a rigid cradle portion structured and arranged to retain the digit, a first biasing device releasably attachable to the cradle portion, a housing portion releasably connectable to the cradle portion, and a plurality of vibrating motors located beneath the cradle portion within the housing portion, such that vibrations translated to the digit enhance blood collection, such that the first biasing device constricts blood flow to the collection point on the digit, causing blood to pool therein, and low frequency and/or high amplitude vibrations cause vasodilation, encouraging blood flow through the capillaries at the collection point.

18 Claims, 7 Drawing Sheets

(56) References Cited

U.S. PATENT DOCUMENTS

| | | | |
|---|---|---|---|
| 9,463,026 B2* | 10/2016 | Corrigan, Jr. | A61B 17/1325 |
| 2003/0181835 A1* | 9/2003 | Klein | A61H 19/34 |
| | | | 601/72 |
| 2003/0220663 A1 | 11/2003 | Fletcher et al. | |
| 2004/0020241 A1* | 2/2004 | Boiadjian | A44C 9/0053 |
| | | | 63/15 |
| 2006/0247493 A1* | 11/2006 | Chen | A61F 5/41 |
| | | | 600/38 |
| 2007/0083131 A1 | 4/2007 | Escutia et al. | |
| 2007/0088385 A1 | 4/2007 | Perry | |
| 2009/0177224 A1 | 7/2009 | Naghavi et al. | |
| 2009/0306468 A1* | 12/2009 | Tasker | A61H 19/34 |
| | | | 600/41 |
| 2010/0004518 A1* | 1/2010 | Vo | A61B 5/14532 |
| | | | 600/310 |
| 2010/0179457 A1 | 7/2010 | Blaine et al. | |
| 2011/0118568 A1 | 5/2011 | Sei | |
| 2011/0166498 A1* | 7/2011 | Shantha | A61B 5/411 |
| | | | 604/20 |
| 2012/0184884 A1* | 7/2012 | Dyer | A61H 19/50 |
| | | | 601/46 |
| 2012/0203141 A1 | 8/2012 | Shantha et al. | |
| 2013/0109914 A1* | 5/2013 | Imboden | A61H 1/00 |
| | | | 600/38 |
| 2015/0257970 A1 | 9/2015 | Mucke et al. | |
| 2018/0369064 A1* | 12/2018 | Baxter | A61F 7/10 |
| 2019/0091598 A1* | 3/2019 | Milanesi | A44C 9/0069 |
| 2019/0099117 A1* | 4/2019 | Pulitzer | A61B 5/150022 |

OTHER PUBLICATIONS

Inal, et al., "Relief of Pain During Blood Specimen Collection in Pediatric Patients" The American Journal of Maternal/Child Nursing, vol. 37, No. 5, 2012, 2 pp. (Abstract Only).

International Search Report and Written Opinion in PCT/IB2019/000271, dated Dec. 19, 2019 12 pages.

* cited by examiner

VIBRATING TOURNIQUET AND METHODS OF COLLECTING BLOOD USING SAME

FIELD OF INVENTION

Devices and methods for collecting blood from a mammalian digit and, more particularly, a vibrating tourniquet for collecting capillary blood from the digit, as well as methods for doing the same are described.

BACKGROUND OF INVENTION

Conventionally, for venous blood collection, a tourniquet may be placed tightly around some portion of an extremity, typically between the subject's heart and the location from which the blood sample is collected or drawn. For example, when drawing blood from the subject's forearm, a tourniquet (e.g., an elastic band) may be placed around the subject's upper arm. The tourniquet restricts the flow of blood to the sampling or drawing location and also makes the veins inside the subject's elbow more pronounced and easier to find and to puncture with a needle.

A similar device does not exist for capillary blood collection, for example from the subject's finger. Typically, finger tourniquets have been used to stop blood flow entirely but not to restrict the flow of blood to the end of the digit where a blood sample is usually collected. Very small volumes of blood (e.g., about 150 µl) may be drawn without using a tourniquet (e.g., using a capillary pipette), but larger volumes of blood are generally not sampled from a subject's fingertip.

Taking a blood sample from a subject's finger using capillary blood collection techniques can also be challenging due to dozens of variables that might reduce capillary blood flow. For example, dehydration, fatigue, lack of exercise, cold weather, and cold hands may reduce blood flow to the collection site. Circulatory disorders, resulting from, for example, obesity, diabetes mellitus, arthritis, disability, heart conditions, and arterial issues, may also cause reduced blood flow to peripheral regions, such as the subject's hands or feet.

BRIEF SUMMARY OF THE INVENTION

Accordingly, it would be desirable to provide a device and method for collecting capillary blood from a mammalian digit (e.g., a human finger) that increase the volume of blood proximate or in the vicinity of the point of blood collection and that, furthermore, encourage blood to flow in the capillaries during the drawing process.

In a first aspect, some embodiments of the present invention include a device for collecting blood from a mammalian digit. In some implementations, the device may include a rigid cradle portion structured and arranged to retain the digit, a first biasing device releasably attachable to the cradle portion and structured and arranged to constrict blood flow in the digit, a housing portion releasably connectable to the cradle portion, and a plurality of vibrating motors located beneath the cradle portion within the housing portion, such that vibrations translated to the digit enhance blood flow. In some variations, the cradle portion may be a vibrating plate that includes a plurality of ribs, while the first biasing device may be any one of an elastic device, an elastic band, a rubber device, a rubber band, and/or a hook and pile combination.

In some applications, the device also may include one or more of the following: a power source(s) (e.g., a battery), a second biasing device (e.g., a spring) located in the housing portion and structured and arranged to bias the vibrating motors against the cradle portion, and/or a processing device adapted to combine vibrations waves from each of the vibrating motors to produce the resulting low frequency wave. In some embodiments, each of the vibrating motors may include a shaft and a weight that is located off center from the shaft, so that the off center weight produces vibration that, in some variations, may be combined to provide a resulting wave characterized as having a low frequency.

In a second aspect, some embodiments of the present invention involve a method of collecting capillary blood from a mammalian digit. In some implementations, the method may include providing a tourniquet device to constrict blood flow in the digit, wherein the tourniquet device may include a rigid cradle portion structured and arranged to retain the digit, a first biasing device (e.g., elastic device, an elastic band, a rubber device, and a rubber band) releasably attachable to the cradle portion, a housing portion releasably connectable to the cradle portion, and a plurality of vibrating motors located beneath the cradle portion within the housing portion. The method may further include: positioning the first biasing device over the digit retained in the cradle portion; releasably attaching the first biasing device to the cradle portion to constrict blood flow in the digit; and producing vibrations by the vibrating motors, such that the vibrations translate to the digit retained in the cradle portion, thereby increasing blood flow into capillaries in the digit for collection.

In some applications, the method may also include controlling the vibrating motors to produce vibrations having a low frequency and/or a high amplitude. In some variations, vibration waves having a high frequency and a high amplitude may be produced by each vibrating motor and, furthermore, these high frequency vibrations may be combined to create a resultant low frequency output.

BRIEF DESCRIPTION OF DRAWINGS

Various features and advantages of the present invention, as well as the invention itself, can be more fully understood from the following description of the various embodiments, when read together with the accompanying drawings, in which.

DETAILED DESCRIPTION OF THE INVENTION

Figure 1:
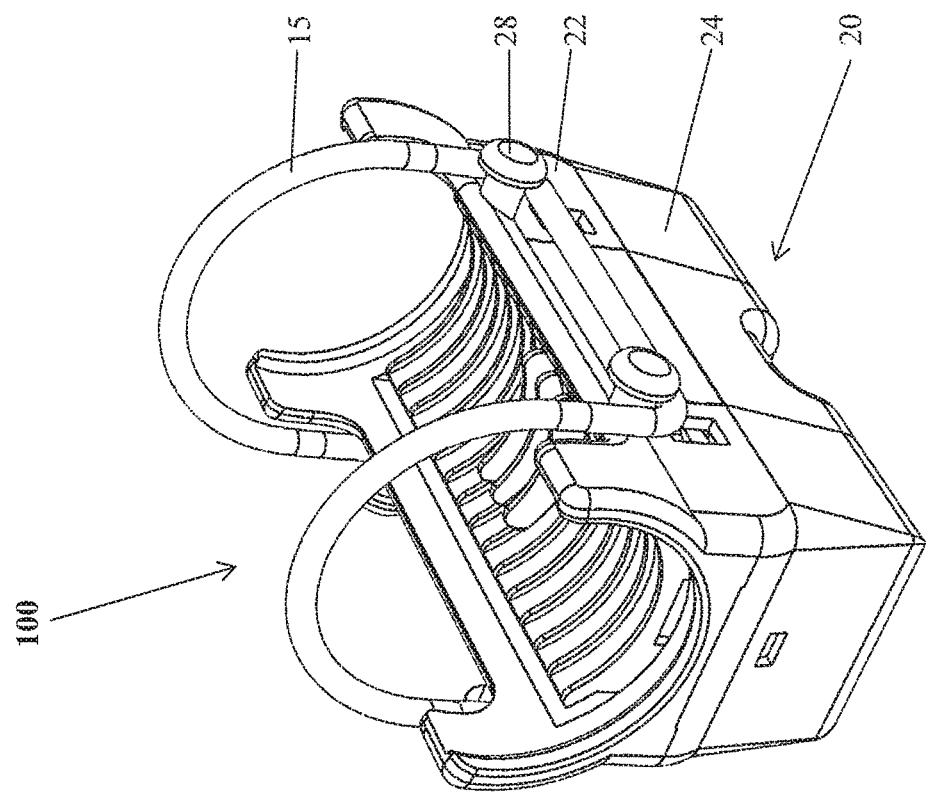
FIG. 1 shows a top perspective view of a device for collecting blood, in accordance with some embodiments of the present invention.

Although the invention will be described in an application for collecting blood from a human fingertip, those of ordinary skill in the art can appreciate that the device and method described herein may be applied to any digit (e.g., toes and fingers) or other appendage of a mammalian subject.

Vibrating Tourniquet for Collecting Blood

Referring to FIGS. 1 through 4, an illustrative embodiment of a vibrating tourniquet for collecting capillary blood from a human digit is shown. In some implementations, the device 100 includes an upper (cradle) portion 10, a biasing element 15, and a lower (housing) portion 20 that are each structured and arranged to accommodate a human finger for the purpose of collecting capillary blood. In some applications, the cradle portion 10 may include an arcuate-shaped substrate 12 made of plastic, metal, or a combination thereof and having a proximal end 14 and a distal end 16. Preferably, the arcuate-shaped substrate 12 is adapted and dimensioned to accommodate all or some portion of a human digit.

In some variations, a vibrating plate 11 includes a plurality of ribs. The ribbed, vibrating plate 11 may provide an interface between the human skin and the vibratory motors. In some variations, the ribbed, vibrating plate 11 is translatable, so that the ribbed, vibrating plate 11 is able to conduct vibrations from vibratory motors to the subject's digit. Moreover, the vibrating plate 11 is ribbed to create greater friction against the skin of the digit. For example, the individual ribs of the ribbed, vibrating plate 11 may be oriented normal, perpendicular, or substantially perpendicular to the longitudinal axis of the cradle portion 10. The ribs of the vibrating plate 11 support and contact portions of the digit, ensuring that the portions of the digit are in and remain in communication with the ribbed, vibrating plate 11. Although the vibrating plate 11 of the present invention is described as being ribbed, those of ordinary skill in the art can appreciate that other patterns and/or textures could be used as an alternative.

Figure 2:
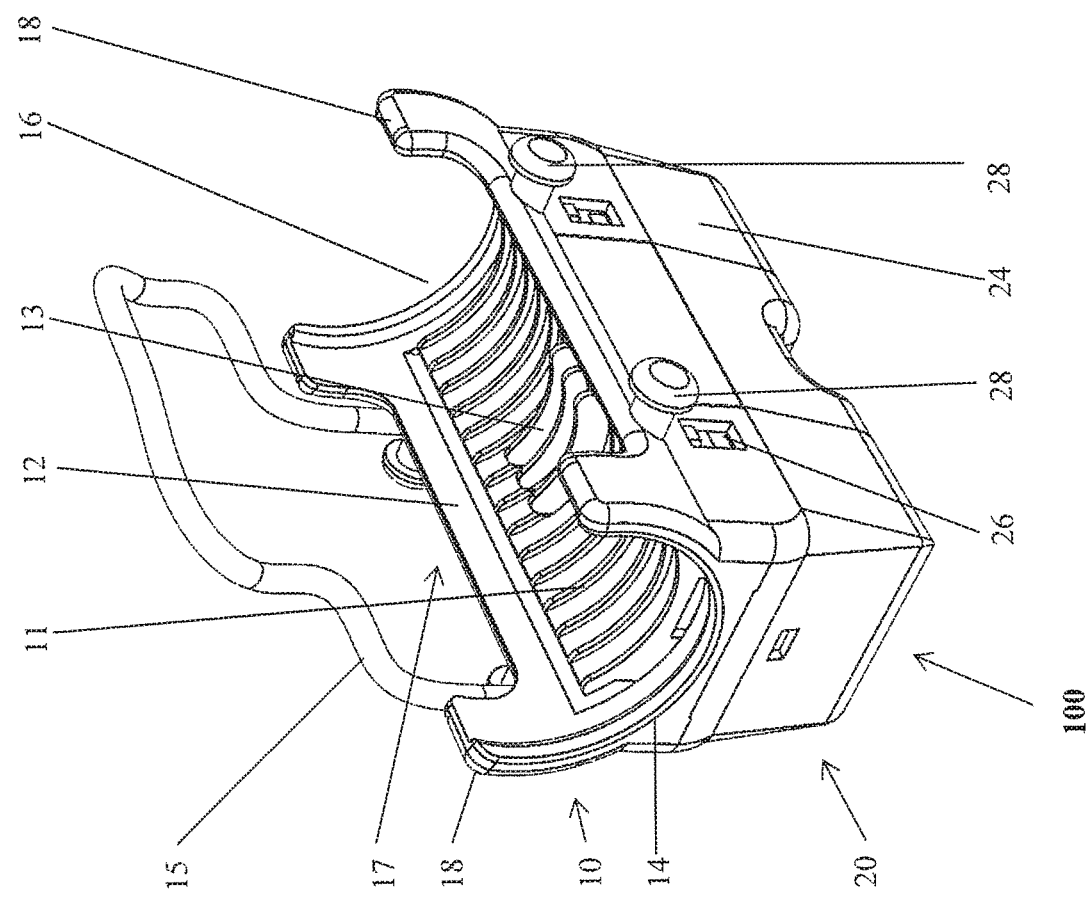
FIG. 2 shows a top perspective view of the device of FIG. 1 with the biasing element attached to each of the attachment posts, in accordance with some embodiments of the present invention.
Figure 4:
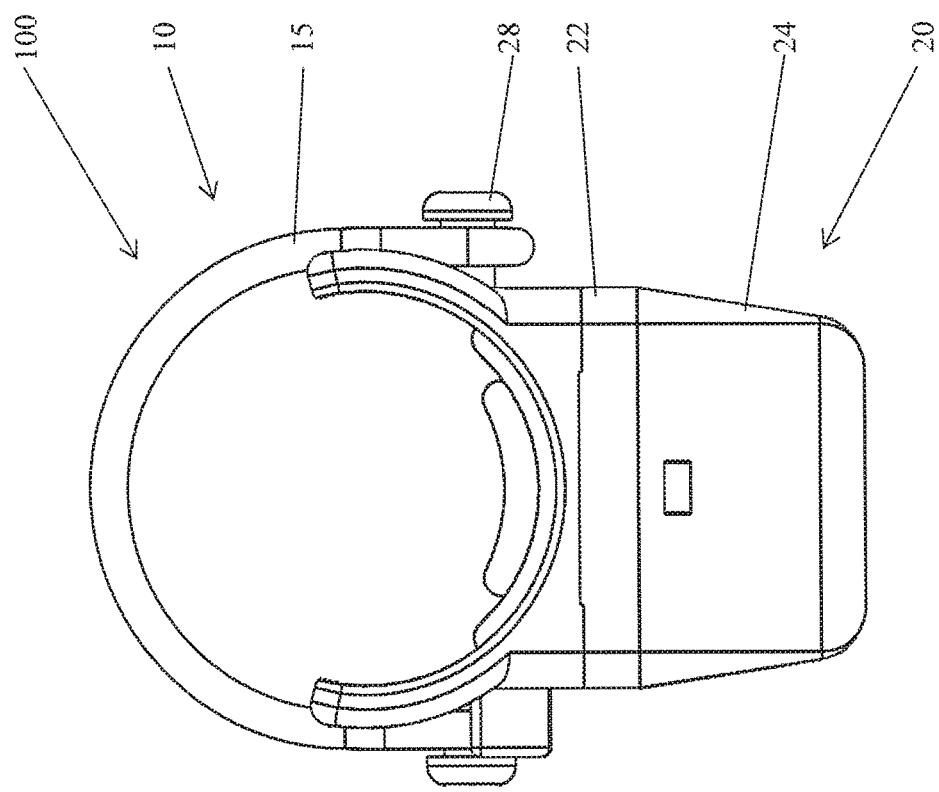
FIG. 4 shows a front view of the device of FIG. 2, in accordance with some embodiments of the present invention.
Figure 3:
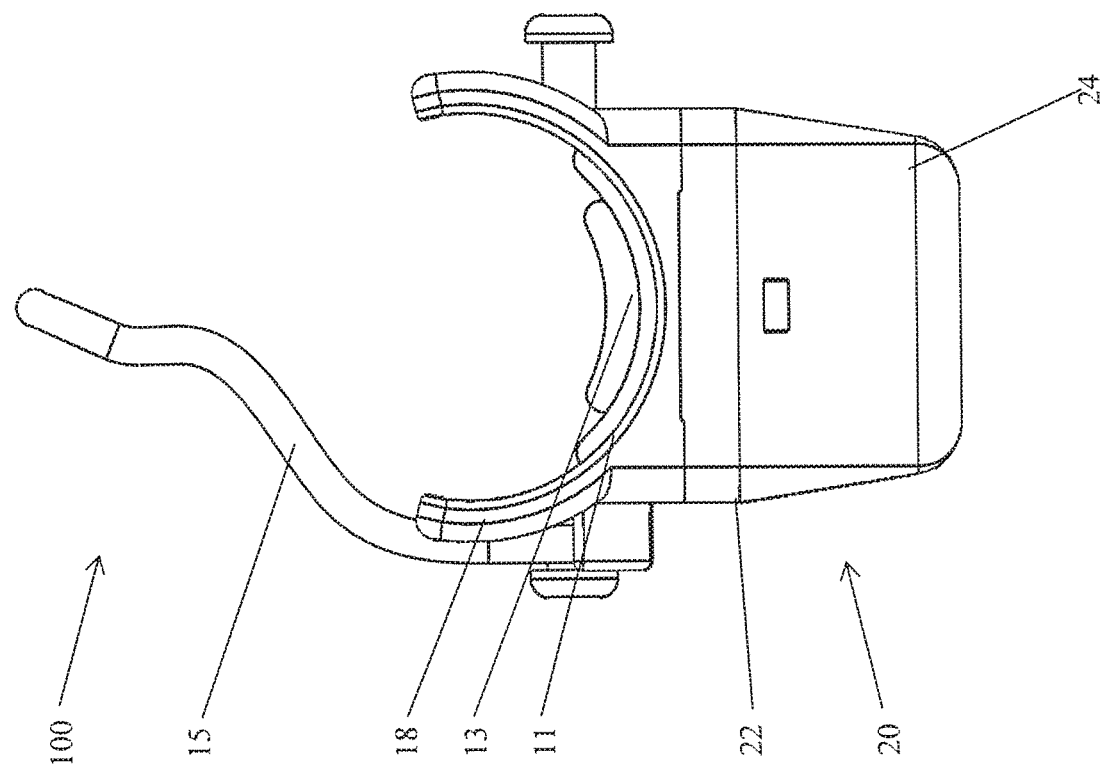
FIG. 3 shows a front view of the device of FIG. 1, in accordance with some embodiments of the present invention.

Optionally, to provide an auto-start capability to turn on the device 100 without having to turn on the device 100 manually, an extended rib portion 13 may be provided through the ribbed, vibrating plate 11. As shown in FIGS. 1 and 2, the extended rib portion 13 may be located within the invert of the arcuate-shaped substrate 12 and, more particularly, the extended rib portion 13 may be located within an opening in the vibrating plate 11 provided therefor. In some variations of the cradle portion 12, when a digit is placed within the device 100, the middle phalanx and/or the proximal phalanx of a finger may cover and contact the extended rib portion 13. Also, as shown in FIGS. 1 and 2, the ribs in the extended rib portion 13 project above the ribs in the vibrating plate 11. This feature ensures that, when a digit is placed in the cradle portion 12, the digit contacts the extended rib portion 13, which will automatically turn on the device 100. More specifically, once the digit contacts the extended rib portion 13, the force applied by the digit on the extended rib portion 13 will force the extended rib portion 13 down, through the opening in the vibrating plate 11. The extended rib portion 13 depresses an ON/OFF button that may be located on a printed circuit board located beneath the vibrating plate 11.

In some applications, projections 18 extend at both ends 14, 16 of and from both sides of the arcuate-shaped substrate 12, so as to produce open sections 17 on both sides of the arcuate-shaped substrate 12. The open sections 17 provide a space for looping the biasing element 15 (e.g., an elastic device, an elastic band, a rubber device, a rubber band, a hook and pile combination, and the like) over the digit, ensuring that the biasing element 15 remains in intimate contact with the digit, so that the biasing element 15 constricts the flow of blood to the fingertip.

In some embodiments, the housing portion 20 may include an upper portion 22 and a lower portion 24. In some variations, the lower portion 24 may be releasably connectable to the upper portion 22 using one or more connecting devices 26 that may be disposed on opposing sides of the housing portion 20. For example, a set (e.g., a pair) of attachment posts 28 may also be fixedly attached on opposing sides of the upper portion 22 of the housing portion 20. In operation, in order to maintain intimate contact between the digit and the biasing element 15 and to ensure that the biasing element 15 constricts the flow of blood to the fingertip, the biasing element 15 may be looped around each of the attachment posts 28 on both sides of the housing portion 20 to place the biasing element 15 in tension. If the biasing element 15 is, in the alternative, a hook and pile combination, a bar may be fixedly attached between the attachment posts 28 on each side of the upper portion 22 of the housing portion 20, such that there is a space formed between the bar and the upper portion 22 of the housing portion 20. One end of the hook and pile combination may be securely attached around the bar on one side of the upper portion. In order to constrict the flow of blood to the fingertip, the free-running end of the hook and pile combination may be inserted in the space between the bar and the upper portion 21 of the housing portion 20; pulled tightly back onto itself to apply pressure to the digit in the cradle portion 12; and the hook portion and pile portion may be brought into contact with one another to maintain the pressure on the digit.

Additional components of the device 100 may be located within the housing portion 20. For example, referring to FIG. 5, the housing portion 20 may include a number of plenum spaces 51, 52, 53. In some implementations, one or more of the plenum spaces 51, 52 may be dimensioned and configured to accommodate a power source 54 (e.g., one or more DC battery), while other plenum space 53 may be dimensioned and configured to accommodate a printed circuit board (PCB) 55, as well as a plurality of (e.g., two) vibrating motors 56a, 56b. Preferably, the vibrating motors 56a, 56b are fixedly attached to the PCB 55 and the PCB 55 is fixedly attached to the ribbed, vibrating plate 11, so that, in operation, the vibrating motors 56a, 56b cause the PCB 55, the vibrating plate 1, and the digit to vibrate. The spring 58 provides some damping such that a majority of the vibrations are carried to the vibrating plate 11 and the finger and very little of the vibrations is directed towards other parts of the device 100.

An ON/OFF button 57 may be provided on the PCB 55, while a second biasing element 58 (e.g., a spring) may be disposed against the underside of the PCB 55. Although an extending rib portion 13 and an ON/OFF button 57 may be provided to provide an auto-start capability, in some variations a conventional ON/OFF switch (e.g., a slider switch, a push switch, and the like) may be provided on the exterior of the housing 20.

In some variations, the PCB 55 may include a processing device (e.g., a microprocessor unit) that is capable of executing a software program, algorithm, driver program and the like stored in memory. In some embodiments, the software program, algorithm, driver program and the like may be adapted to control the frequency and/or amplitude of the vibrations produced by each motor 56a, 56b, thereby defining the final beating frequency output. The PCB 55 may also include other hardware and/or software for driving the motors 56a, 56b, voltage regulators, and other circuit protection components on the PCB 55.

Figure 5:
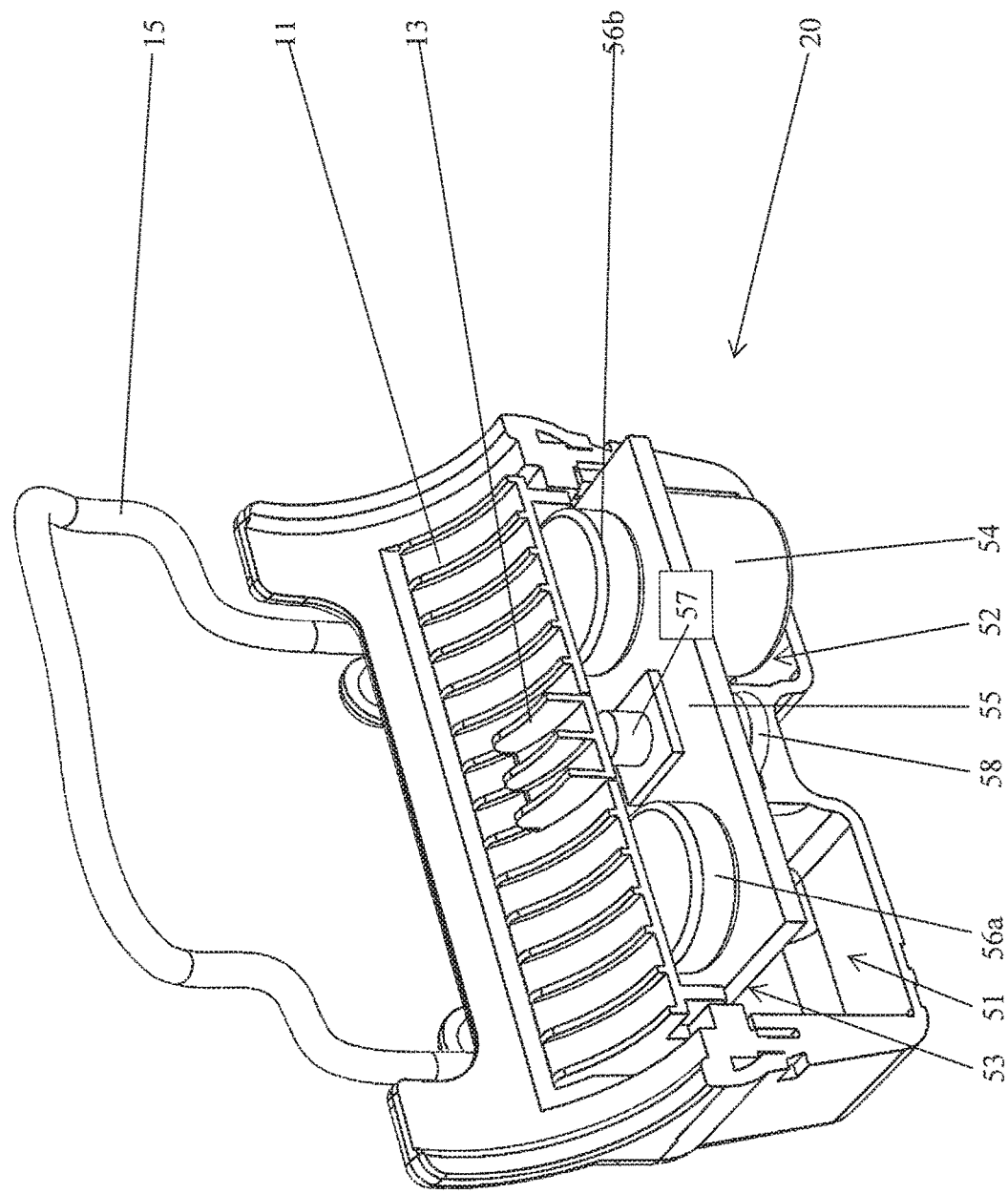
FIG. 5 shows a cross sectional view of the device of FIG. 1, in accordance with some embodiments of the present invention.

As shown in FIG. 5, the extended rib portion 13 and ribbed, vibrating plate 11 may be configured to translate freely up and down within the arcuate-shaped substrate 12 of the cradle portion 10. As a result, once a digit is placed against the extended rib portion 13, the extended rib portion 13 is structured and arranged to displace (e.g., in a downward direction) with respect to the vibrating plate 11, further depressing the ON/OFF button 57 sufficiently to turn on the PCB 55 and/or cause the PCB 55 to execute a start-up program. Moreover, as the digit is further pushed into the cradle portion 10, force from the digit may cause the ribbed, vibrating plate 11 to displace (e.g., in a downward direction) with respect to the arcuate-shaped substrate 12 of the cradle portion 10. Such displacement of the ribbed, vibrating plate 11 will also force the PCB 55 down against the spring 58.

The spring 58 may be adapted to ensure that, during vibration, the vibrating motors 56a, 56b stay in intimate contact with the ribbed, vibrating plate 11 and, moreover, that the ribbed, vibrating plate 11 remains in intimate contact with the digit in the cradle portion 10. There can be a single spring 58 (as shown) or multiple springs 58 used in the device 100. In operation, once the biasing element 15 exerts pressure onto the digit, the translating vibrating plate 11 compresses both the ON/OFF switch 57 and the spring 58. The spring constant in the spring 58 will tend to resist this compressive force, causing the spring 58 to push the PCB 55, the vibrating motors 56a, 56b, and the ribbed, vibrating plate 11 against the skin of the digit. This spring-loaded mechanism ensures that the resistive force with which the ribbed, vibratory plate 11 is pressed against the digit is governed by the force of the spring 58 and not by how tightly the device 100 has been tightened around the finger using the biasing element 15. This prevents overtightening of the ribbed, vibratory plate 11 against the skin of the digit, which could lead to total cut-off of blood supplied to the finger.

Figure 6:
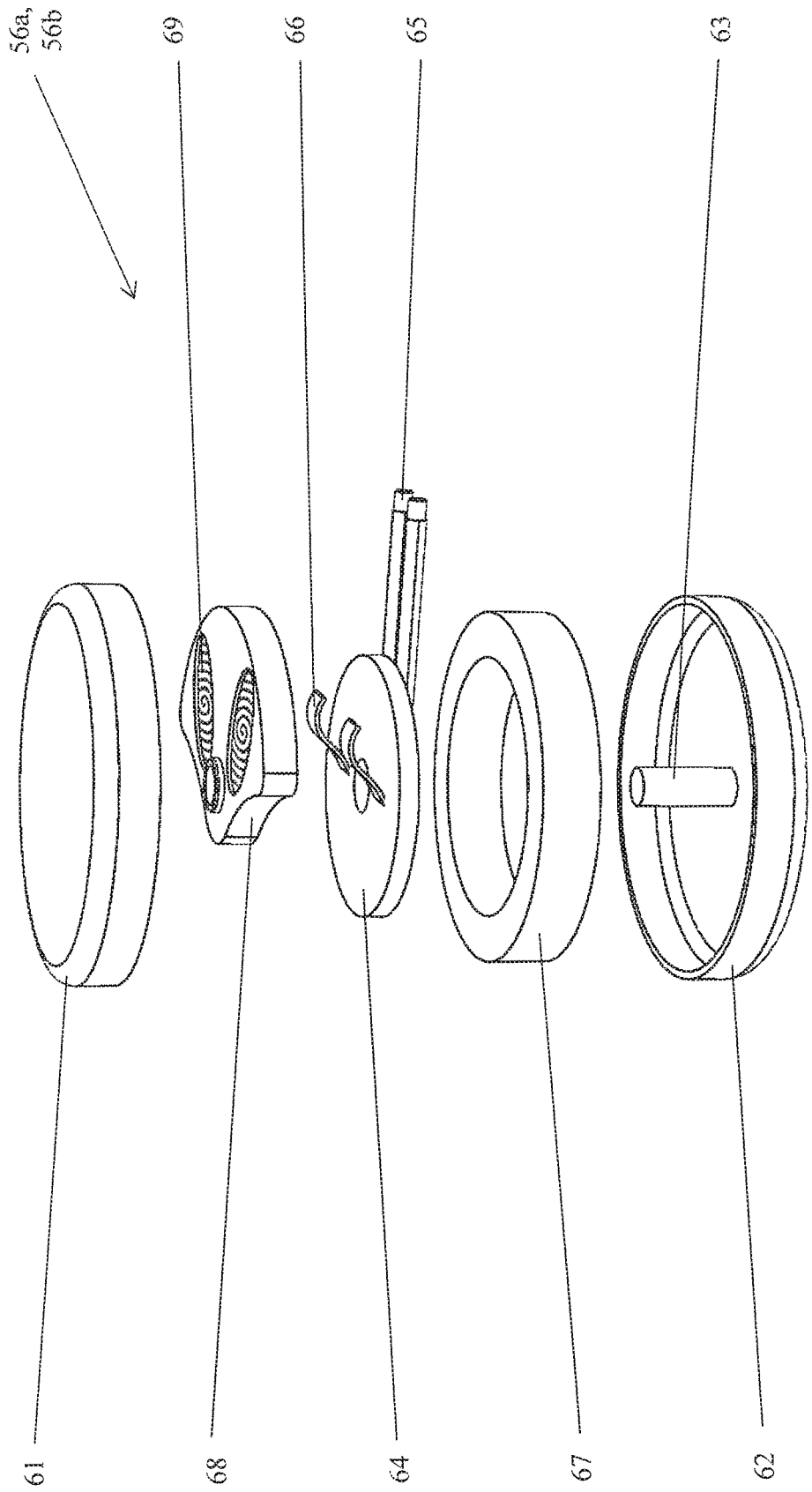
FIG. 6 shows an exploded view of a coin-type vibrating motor, in accordance with some embodiments of the present invention.

In some embodiments, once the PCB 55 and device 100 have started up properly, the PCB 55 may include one or more software programs, algorithms, driver programs, and the like to cause the plurality of vibrating motors 56a, 56b to generate vibrations in a desired manner and fashion. More particularly, it may be desirable for the vibrating motors 56a, 56b to generate vibrations in a beating phenomenon or at a beating frequency. An exemplary, coin-type vibrating motor 56a, 56b suitable for use with the device 100 is shown in FIG. 6. In some embodiments, the vibrating motors 56a, 56b may include an upper casing 61 and a lower casing 62, the lower casing including a shaft 63. A substrate 64 that includes a printed circuit board may be configured to include an opening adapted to fit over the shaft 63. Power for running the motors 56a, 56b may be provided to components on the substrate via an electrical bus on the PCB 55 or, in the alternative, power may be provided directly from the power source 54, e.g., via electrical leads 65 from the power source 54 to the motors 56a, 56b. A pair of brushes 66 may be located on the substrate 64. A magnet 67 may be adapted to surround the brushes 66. An imbalanced weight 68 having a plurality of coil assemblies 69 may be placed over the shaft 63 and atop the magnet 67. In operation, the brushes 66 provide power selectively or alternately to the coil assemblies 69, thereby alternating the direction of a magnetic field induced by current flowing through the coil assemblies 69. The induced magnetic field interacts with the magnetic flux from the magnet 67. The alternating direction of the induced magnetic field and the interaction between the induced magnetic field and the magnetic flux cause the imbalanced weight 68 to rotate about the shaft 63. Due to an off-center mass in the imbalanced weight 68, the rotating imbalanced weight 68 produces wobble and vibrations.

Although the figures show an embodiment that includes two motors 56a, 56b, this is done for illustrative purposes only. Performance may further be improved by using more than two motors 56a, 56b to enhance the beating effect. In some instances, it may also be possible to produce a desired beating phenomenon use a single motor having a mechanism coupled to the motor's shaft. Such an arrangement would work more like a car's gearbox, which increases or reduced the output speed and torque mechanically rather than electronically.

Method of Drawing Blood

Figure 7:
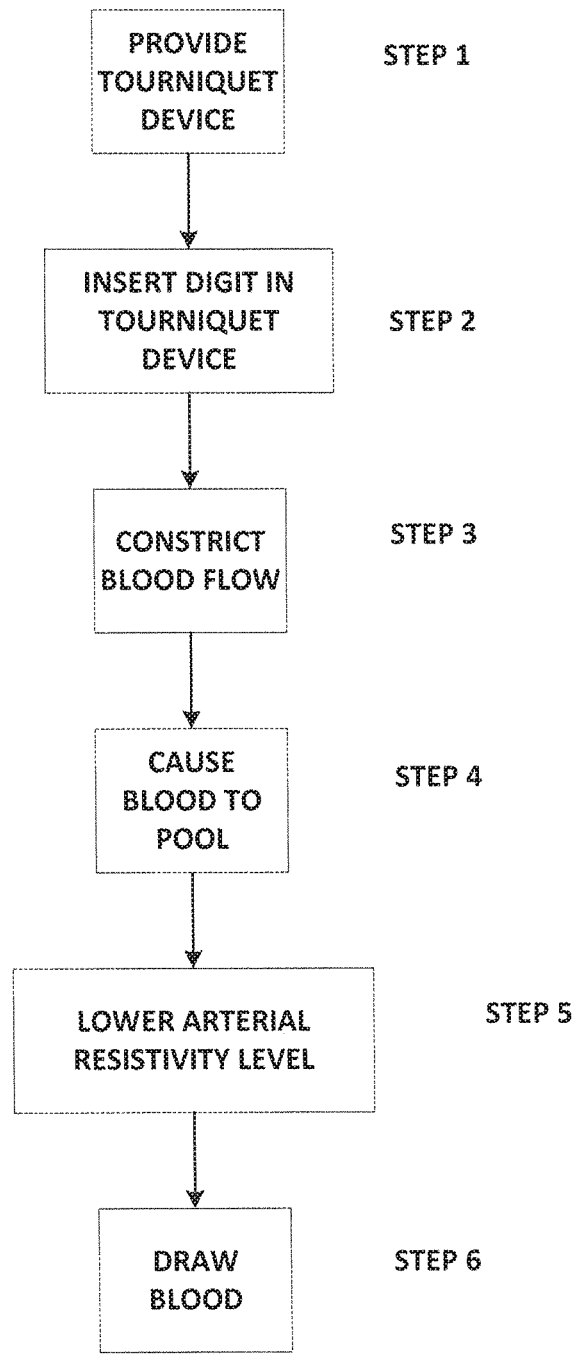
FIG. 7 shows a flow chart of a method of drawing blood, in accordance with some embodiments of the present invention.

Having described a device for use in collecting or drawing capillary blood from a fingertip of a mammalian subject, a method of drawing blood using the device will now be described. Referring to FIG. 7, in some embodiments, a method of drawing capillary blood from the fingertip of a mammalian subject may include promoting blood to pool proximate to or in the vicinity of the drawing site and, moreover, encouraging the pooled blood to flow into the capillaries from which the blood sample will be taken or drawn. Promoting blood to pool proximate to or in the vicinity of the drawing site can include, for example, constricting blood flow in the digit, while encouraging the pooled blood to flow into the capillaries may involve lowering the arterial resistivity index. The previously described device provides each of these desirable qualities.

Accordingly, in a first step, a tourniquet device similar to the one previously described may be provided (STEP 1) and the digit, from whence the capillary blood sample will be drawn, maybe placed in the tourniquet device (STEP 2).

Figure 8:
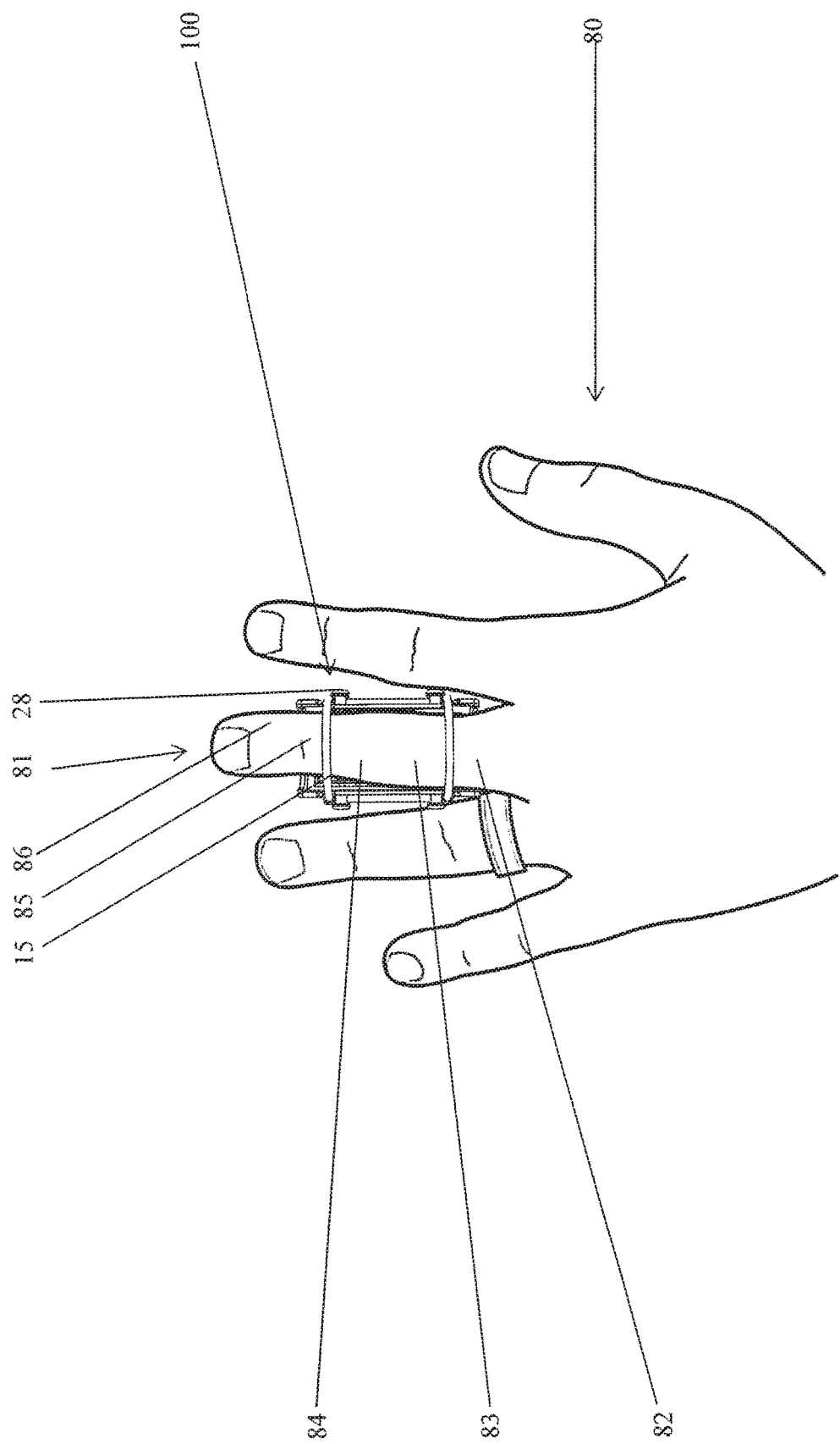
FIG. 8 shows a middle finger inserted in the device of FIG. 1, in accordance with some embodiments of the present invention.

For example, FIG. 8 shows a tourniquet device 100 disposed on the middle finger 81 of a subject's left hand 80. In particular, the proximal 82 and middle phalanxes 84 of the subject's middle finger 81 may be placed in the cradle portion 10 of the device 100 (STEP 2), such that the proximal interphalangeal joint 83 is resting on some portion of the extended rib portion 13. The distal phalanx 86 and distal interphalangeal joint 85 may be substantially out of the cradle portion 10 of the device 100. The biasing element 15 may then be stretched over each of the attachments posts 28, so that the tension in the biasing element 15 restricts (i.e., constricts or partially blocks) blood flow in the middle finger 81 (STEP 3).

More specifically, the rigid ribbed, vibrating plate 11 on which the finger 81 is placed and the more elastic biasing element 15 across the top of the finger 81 constrict or partially block the flow of blood out of the finger 81 without completely cutting off blood supply to the finger 81. Due to the higher arterial blood pressure relative to the lower venous blood pressure and the constriction afforded by the biasing element 15, the rate at which blood enters the finger 81 exceeds the rate at which blood exits the finger 81, causing blood to pool in the finger 81 proximate or in the vicinity of, for example, the distal phalanx 86.

Capillaries are extremely tiny blood vessels. However, low frequency vibrations have been used to promote dilation in capillaries, resulting in more red blood cells entering the capillaries. Furthermore, vibrations that have low frequency and high amplitude typically increase the deformability of the cell walls of red blood cells, making it easier for blood cells to squeeze into a tiny capillary. Accordingly, subjecting the pooling blood to low frequency and/or high amplitude vibrations promotes greater blood flow (STEP 5) into the dilated capillaries. Indeed, vibrations that have a low frequency and/or a high amplitude lower the arterial resistivity index, i.e., the resistive force that a microvascular bed applies to the blood which is flowing through it, making it easier for blood to flow to areas of the body where there is less blood supply. Low frequency vibrations also cause vasodilation, i.e., a widening of the blood vessels.

In some instances, creating low frequency vibrations is simple, especially using large mechanical devices, such as gearboxes, levers, shafts, and so forth. In small, compact devices, however, such mechanical systems cannot be used because of lack of space, weight restriction, and/or associated costs. Thus, beating phenomenon (also known as beating frequency or simply beats) may be employed to combine multiple (e.g., two) high frequency (e.g., vibratory) waves to create a resultant low frequency output. The phenomena by which two high frequencies (e.g. vibratory) waves enforce each other or cancel out each other are referred to, respectively, as constructive interference and destructive interference, which is shown in FIG. 9.

Figure 9:
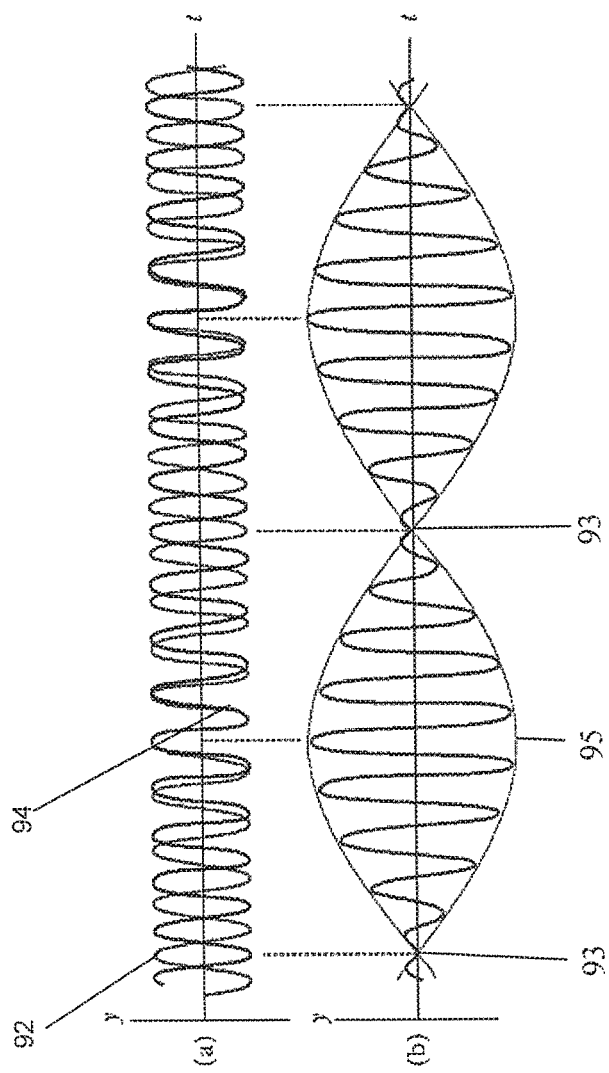
FIG. 9 shows constructive and destructive interference of a vibratory wave, in accordance with some embodiments of the present invention.

The upper displacement versus time relationship (labeled (a)) in FIG. 9 shows two high frequency (e.g., vibratory) waves 92, 94 being overlapped on each other. Typical waves 92, 94 generated by small vibratory motors may be characterized as having slightly different (high) frequencies but having the same or substantially the same relatively high amplitudes. As shown in the lower relationship (labeled (b)) in FIG. 9, at certain instances 93, when the two relatively high amplitude, high frequency waves 92, 94 are combined, e.g., by a processing device, the resultant wave may be characterized as a high amplitude, low frequency wave. Indeed, in some implementations, the processing device may be adapted to combined two waves 92, 94, such that, in the resultant wave, at certain instances 93, the combined waves 92, 94 cancel each other out, while at other instances 95, the combined waves 92, 94 enforce each other. The net effect of this constructive and destructive interference results in a high amplitude, low frequency wave. In short, the beating phenomenon enables a transfer of energy into the system where low-frequency vibrations can be induced by coupling vibrations from multiple (e.g., two) high-frequency sources.

With a sufficient supply of blood in the fingertip, after lancing, an ample amount of blood may be collected (STEP 6) using techniques that are well known to the art.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions can be made by those skilled in the art without departing from the spirit and scope of the invention. Accordingly, the appended claims shall not be limited by the particular features that have been shown and described, but shall be construed also to cover any obvious modifications and equivalents thereof.

What we claim is:

1. A device for collecting blood from a mammalian digit, the device comprising:
    a cradle portion comprising a rigid, arcuate-shaped substrate comprising a vibrating plate disposed in an invert thereof, wherein a plurality of ribs are formed on the vibrating plate in the invert of the rigid substrate and oriented perpendicular or substantially perpendicular to a longitudinal axis of the rigid substrate, the rigid substrate and plurality of ribs structured and arranged to support the digit;
    an extended rib portion that is translatable through an opening in the vibrating plate;
    a first biasing device releasably attachable to the cradle portion and structured and arranged to constrict blood flow in the digit;
    a housing portion releasably connectable to the cradle portion; and
    a plurality of vibrating motors coupled to the vibrating plate and located beneath the cradle portion within the housing portion, wherein vibrations translated to the digit enhance blood flow.

2. The device of claim 1, wherein the first biasing device is selected from the group consisting of an elastic device, an elastic band, a rubber device, and a rubber band.

3. The device of claim 1, wherein the first biasing device comprises a hook and pile combination.

4. The device of claim 1 further comprising at least one power source.

5. The device of claim 4, wherein the power source is a battery.

6. The device of claim 1 further comprising a second biasing device located in the housing portion and structured and arranged to bias the vibrating motors against the cradle portion.

7. The device of claim 6, wherein the second biasing device comprises a spring.

8. The device of claim 6, wherein the second biasing device is structured and arranged to bias the vibrating motors against the vibrating plate of the cradle portion.

9. The device of claim 1, wherein each of the vibrating motors comprises a coin-type vibrating motor.

10. The device of claim 1, wherein each vibrating motor generates a vibration wave that can be combined to provide a resulting wave having a frequency lower than a frequency of the vibration wave of each vibrating motor.

11. The device of claim 10 further comprising a processing device that is adapted to combine vibration waves from each of the vibrating motors to produce the resulting wave.

12. The device of claim 1, wherein the extended rib portion projects above the plurality of ribs.

13. The device of claim 1 further comprising an ON/OFF switch in operative contact with the extended rib portion.

14. The device of claim 1, wherein the housing portion comprises a plurality of attaching posts about which the first biasing device is looped.

15. A method of collecting capillary blood from a mammalian digit, the method comprising:
    providing the device of claim 1 to constrict blood flow in the digit;
    positioning the first biasing device over the digit retained in the cradle portion; releasably attaching the first biasing device to the cradle portion to constrict blood flow in the digit; and
    producing vibrations by the vibrating motors, such that the vibrations translate to the digit retained in the cradle portion, thereby increasing blood flow into the capillaries in the digit for collection.

16. The method of claim 15, wherein the first biasing device is selected from the group consisting of an elastic device, an elastic band, a rubber device, and a rubber band.

17. The method of claim 15, wherein producing vibrations comprises producing by each vibrating motor a respective vibration wave having a frequency and an amplitude.

18. The method of claim 17 further comprising combining a plurality of frequency vibrations generated by each vibrating motor to create a resultant frequency output having a frequency lower than the frequency of the respective vibration wave of each vibrating motor.

* * * * *